(12) United States Patent
Marino et al.

(10) Patent No.: US 6,519,319 B1
(45) Date of Patent: Feb. 11, 2003

(54) IMAGE INTENSIFIER RETICLE SYSTEM

(75) Inventors: James F. Marino, La Jolla, CA (US); Troy Wooley, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/696,923

(22) Filed: Oct. 25, 2000

Related U.S. Application Data (63) Continuation-in-part of application No. 09/326,740, filed on Jun. 4, 1999, now Pat. No. 6,266,394.
(60) Provisional application No. 60/120,663, filed on Feb. 19, 1999.

(51) Int. Cl.⁷ .................................................. H05G 1/28
(52) U.S. Cl. ........................................ 378/162; 378/163
(58) Field of Search .............................. 378/162, 163, 378/164, 165, 204, 205, 207

(56) References Cited

U.S. PATENT DOCUMENTS

| | | | |
|---|---|---|---|
| 3,128,768 A | 4/1964 | Geistauts | |
| 4,696,308 A | 9/1987 | Meller et al. | |
| 4,722,336 A | 2/1988 | Kim et al. | |
| 4,756,309 A | 7/1988 | Sachse et al. | |
| 5,189,690 A | 2/1993 | Samuel | |
| 5,235,528 A | * 8/1993 | Silver et al. | 250/363.09 |
| 5,239,569 A | * 8/1993 | Saleh et al. | 378/163 |
| 5,324,300 A | 6/1994 | Elias et al. | |
| 5,330,488 A | 7/1994 | Goldrath | |
| 5,336,880 A | * 8/1994 | Leclerc et al. | 250/214 VT |
| 5,484,437 A | 1/1996 | Michelson | |
| 5,488,958 A | 2/1996 | Topel et al. | |

* cited by examiner

*Primary Examiner*—David P. Porta
(74) *Attorney, Agent, or Firm*—Jonathan Spangler, Esq.

(57) ABSTRACT

A method of aligning a C-arm of an image intensifier for rotation in a selected plane, the C-arm having a transmitter mounted at one end and a receiver mounted at an opposite end, comprising: identifying the selected plane by viewing the location of bony structures with the image intensifier; and aligning indicia disposed on a radio-opaque reticle covering at least a portion of the receiver with the selected plane, the indicia being aligned with the plane of rotation of the C-arm, thereby aligning the plane of the C-arm with the selected plane.

1 Claim, 9 Drawing Sheets

IMAGE INTENSIFIER RETICLE SYSTEM

CROSS-REFERENCES TO RELATED APPLICATIONS

The present application is a continuation-in-part of U.S. Provisional Patent Application Ser. No. 09/326,740, filed Jun. 4, 1999 now U.S. Pat. No. 6,266,394 which is a regular application claiming benefit under 35 USC §119(e) from U.S. Provisional Patent Application Ser. No. 60/120,663 filed Feb. 19, 1999; the complete disclosures of which are hereby incorporated by reference in their entirety for all purposes.

TECHNICAL FIELD

The present invention relates to reticle designs for C-arm surgical image intensifiers.

SUMMARY OF THE INVENTION

The present invention provides reticle systems for attachment to an image intensifier and methods of use which allow a standard C-arm image intensifier to be easily aligned to rotate in a selected plane about any desired point in a human body. The present invention can be used to align an image intensifier to rotate in any plane through the human body, wherein the plane is preferably defined by viewing bones or other radio-opaque structures in the body with the image intensifier system. Although the present invention can be aligned to rotate the C-arm in any desired plane passing through a human body, the present invention is ideally suited to align a conventional C-arm image intensifier to rotate in a plane passing between two adjacent vertebrae in a patient's spine. It is to be understood, however, that the present invention is not so limited to alignment of C-arm image intensifiers only with respect to intervertebral planes.

After aligning the orientation of the image intensifier with the selected intervertebral plane, the image intensifier can be rotated about a selected point to provide both lateral and anterior-posterior views through the patient while remaining in the selected intervertebral plane.

The present invention also provides an improved reticle having indicia which can be easily aligned with opposing vertebral end plates such that the reticle can be used to align a C-arm image intensifier with a patient's intervertebral plane.

In accordance with an aspect of the present invention, a surgical instrument can be advanced into the patient such that it passes between a pair of parallel indicia lines, with the instrument being guided along a preferred plane into the patient.

In accordance with another aspect of the invention, the present reticle provides indicia which do not cross over one another at the center of the reticle. An advantage of such a design is that the surgeons' view is not obstructed at the operative site by any line or cross hair passing over the center of the reticle.

DESCRIPTION OF THE SPECIFIC EMBODIMENTS

Figure 1:
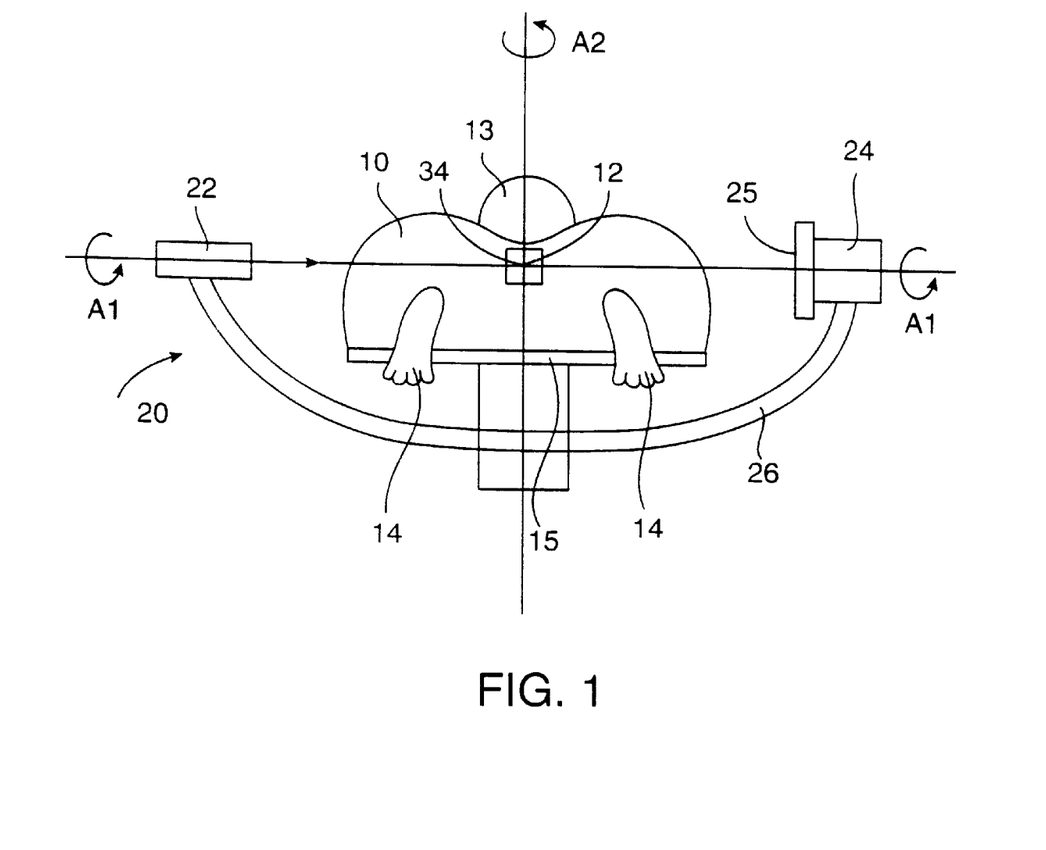
FIG. 1 is a rear elevation view of a prone lying patient with an image intensifier taking a lateral view through the patient.
Figure 2:
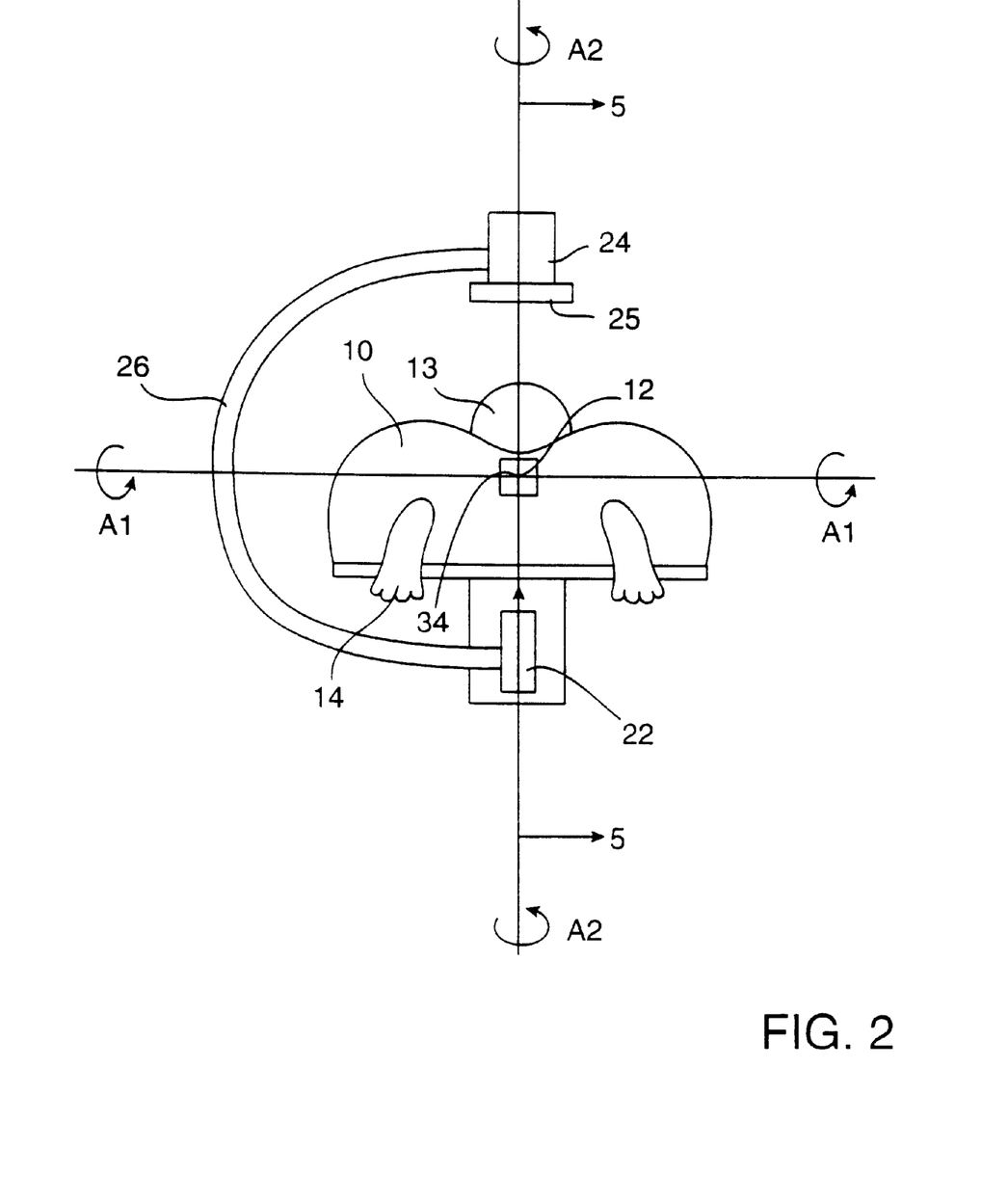
FIG. 2 is a view corresponding to FIG. 1, but with the image intensifier taking an anterior-posterior view through the patient.
Figure 7:
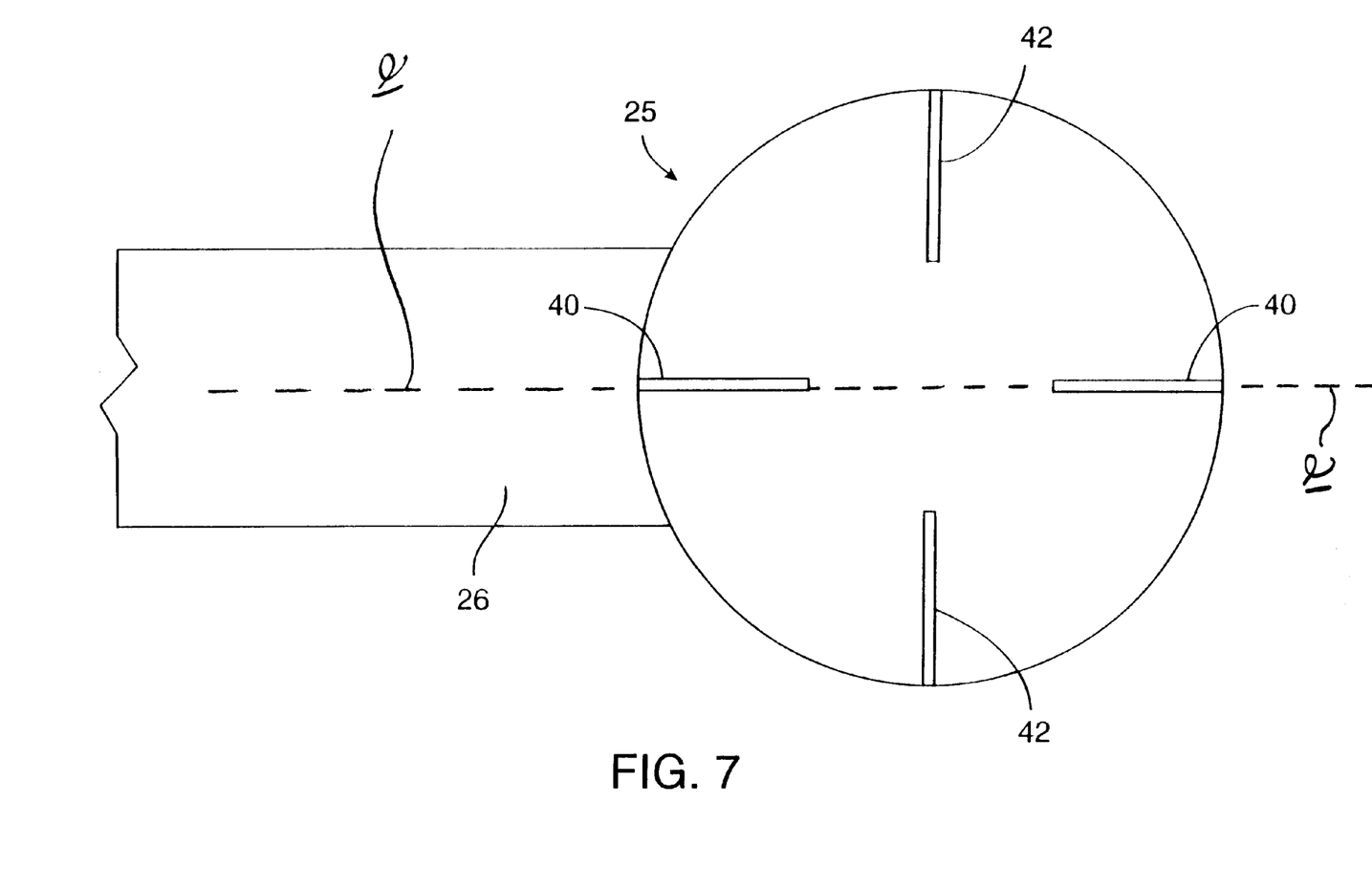
FIG. 7 is an end view of a reticle of the present invention as attached over the receiving end of the image intensifier.

Referring first to FIG. 1, a patient 10 having a spine 12, head 13 and feet 14 is positioned in a prone lying manner on a radiotransparent table 15. A conventional image intensifier 20 having an emitter 22 and a receiver 24 which are together held on opposite sides of the patient by a standard C-arm 26 is positioned as shown in FIG. 1 to generate a lateral radio-image view through the patient. As is shown in FIG. 2, C-arm 26 can also be rotated so as to provide an anterior-posterior image through the patient. (Preferably, C-arm 26 is rotated in plane 21 as shown in FIG. 7 when moving from the position of FIG. 1 to the position of FIG. 2).

C-arm image intensifier 20 may comprise any standard image intensifier, preferably having the property that rotation 24 of C-arm 26 in plane 21 of the C-arm (such as from the orientation in FIG. 1 to that of FIG. 2), causes the image intensifier to rotate about a fixed point in space equidistant between emitter 22 and a receiver 24.

In a preferred aspect of the present invention, C-arm 26 is aligned to rotate in a preferred plane about a desired point in space positioned equidistant between emitter 22 and a receiver 24.

In an exemplary aspect of the invention, the desired point in space is disposed within the patient's intervertebral space and the desired plane is an intervertebral plane which passes between adjacent vertebrae, as follows.

Figure 5:
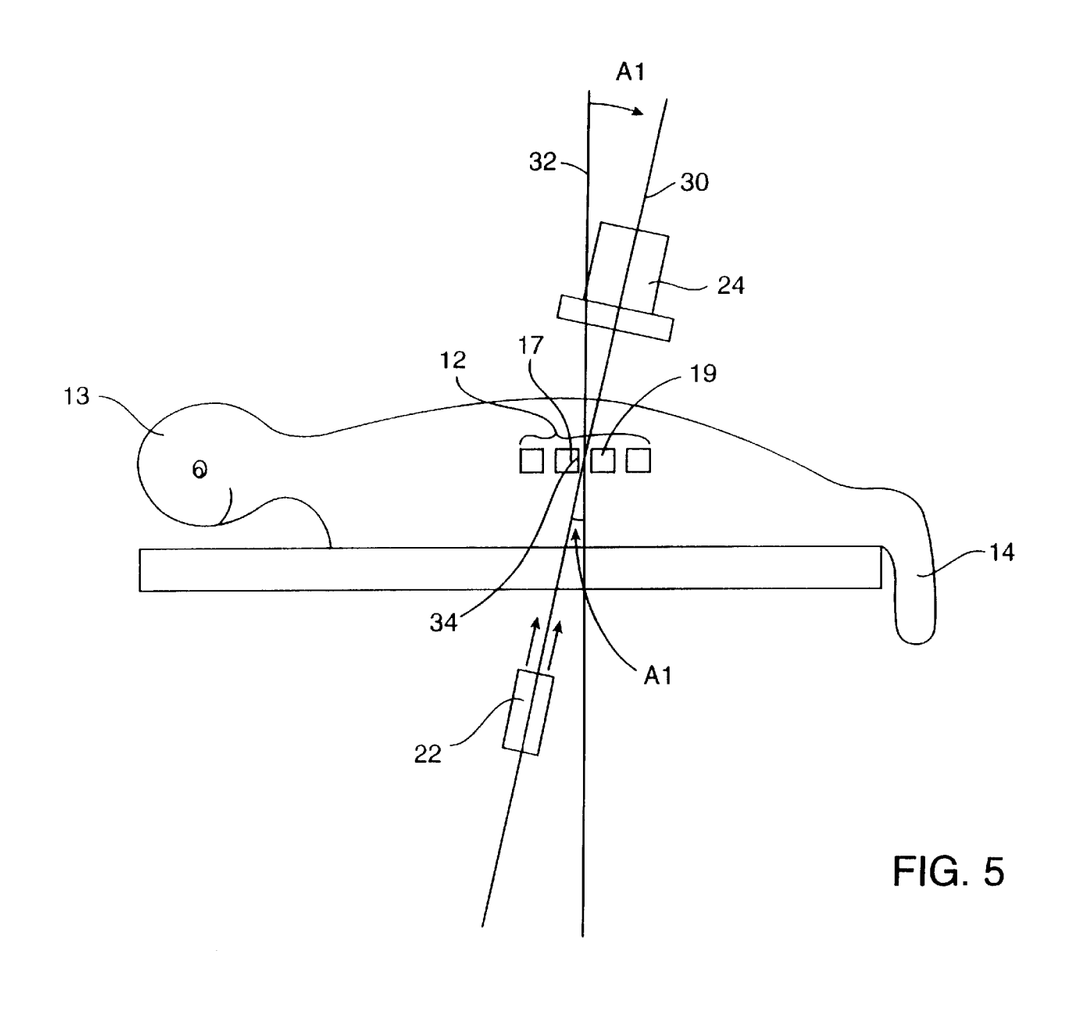
FIG. 5 is a sectional side elevation view taken along line 5—5 in FIG. 2.

When taking either lateral or an anterior-posterior images of adjacent vertebrae in the patient's spine, as seen in FIGS. 1 and 2, respectively, it is preferred to take such images along a plane which passes between the adjacent vertebrae. However, each pair of adjacent vertebrae in the patient's spine will have a different intervertebral plane due to the natural lordosis in the patient's spine. For example, as is seen in FIG. 5, spine 12 comprises adjacent vertebrae 17 and 19. Each pair of adjacent vertebrae in the spine will each have a unique intervertebral plane passing therethrough. For example, intervertebral plane 30 will pass between vertebrae 17 and 19, as shown. Accordingly, considerable adjustment of the image intensifier orientation is required to align it with the selected intervertebral plane. These alignment problems are further complicated when attempting to rotate the image intensifier from a lateral position to an anterior-posterior position.

In a preferred aspect, the present invention may be used to align C-arm 26 image intensifier 20 with intervertebral plane 30 such that as the image intensifier is moved from the position shown in FIG. 1 to the position shown in FIG. 2, C-arm 26 of image intensifier 20 remains at all times disposed in the intervertebral plane 30, as follows.

Figure 3:
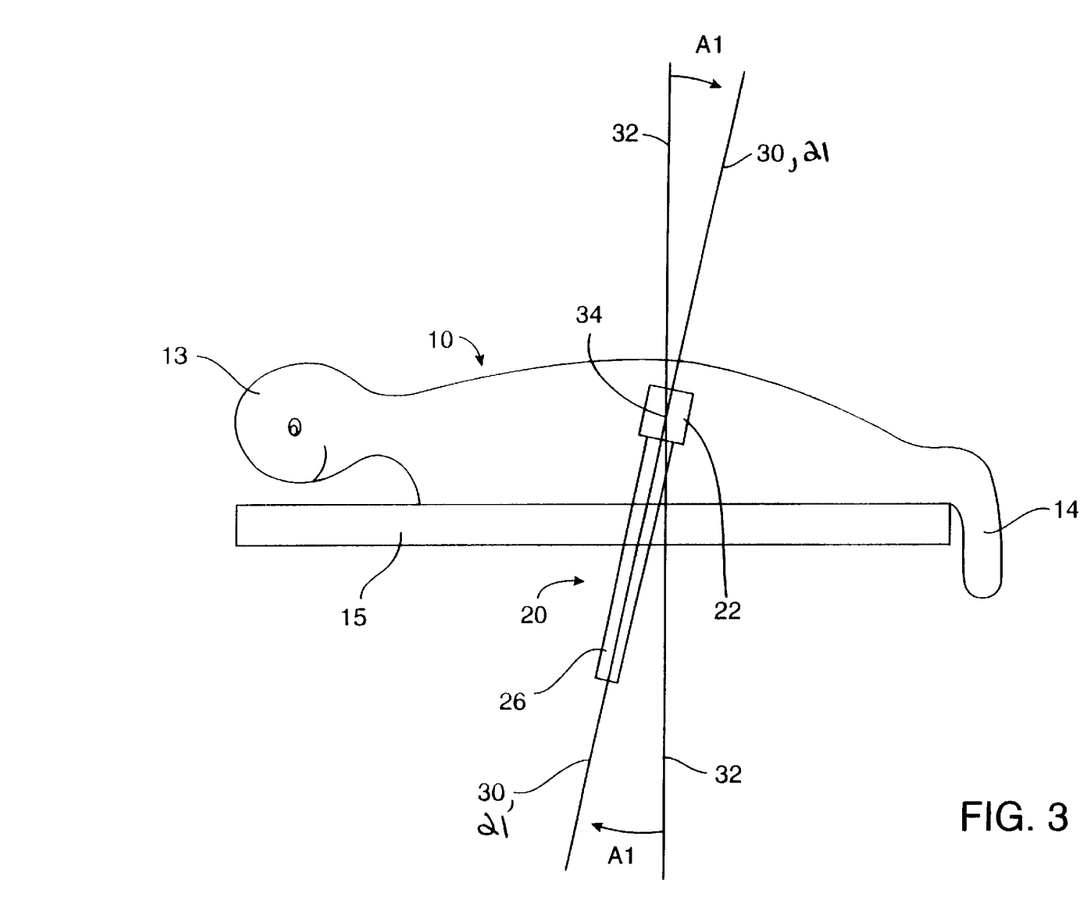
FIG. 3 is a side elevation view corresponding to FIG. 1.
Figure 4:
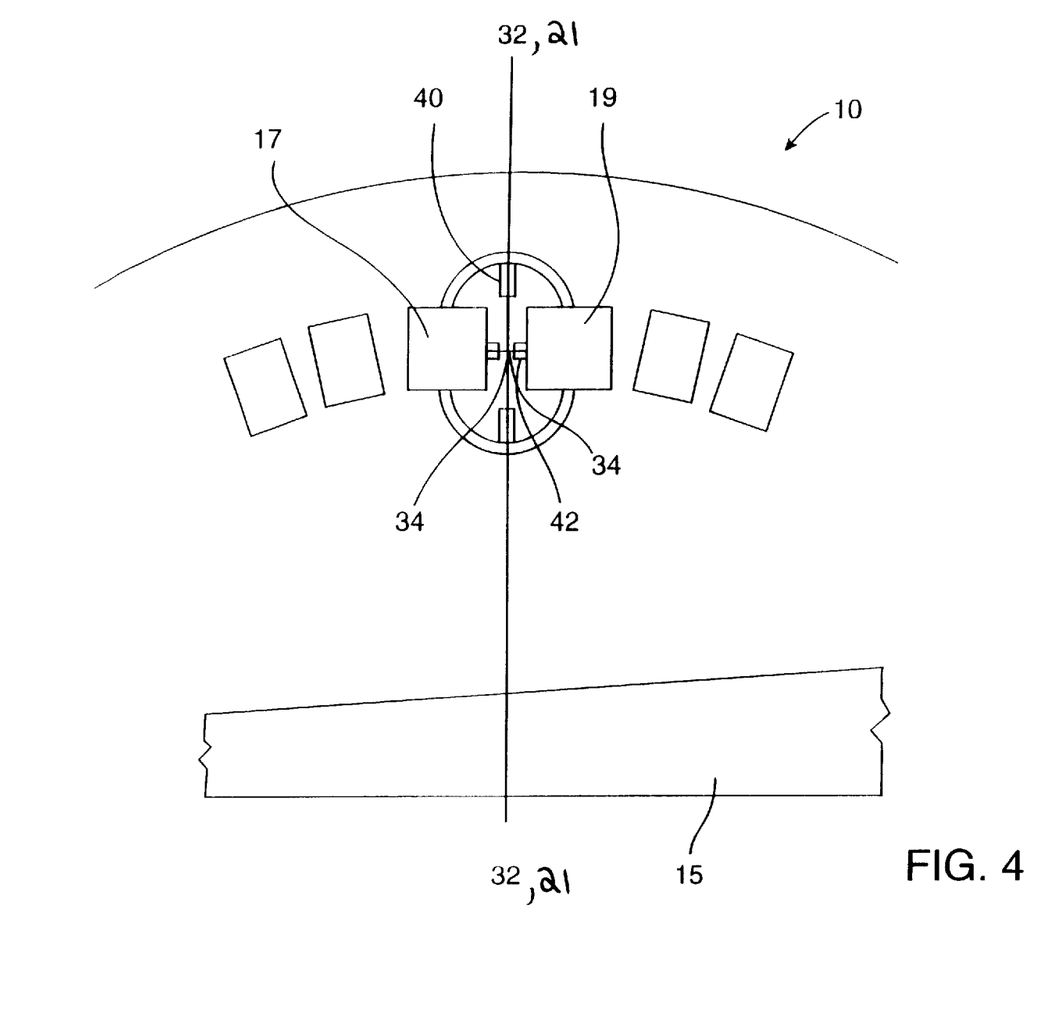
FIG. 4 is a view of an image taken by the image intensifier with the image intensifier being positioned as shown in FIGS. 1 and 3.

As can be seen in FIGS. 3 and 5, the positioning of the image intensifier 20 to align C-arm 26 with a selected intervertebral plane 30 will require C-arm 26 to be rotated by angle A1 to a vertical plane 32. The point 34 about which image intensifier 20 is pivoted should preferably be between adjacent vertebrae 17 and 19, (as determined by viewing the lateral image through the patient as shown in FIG. 4 as will be explained). Image intensifier 20 is preferably initially positioned about the patient such that point 34 will be disposed equidistant between emitter 22 and a receiver 24. Accordingly, rotation of C-arm 26 in plane 30 will be about point 34 with point 34 remaining equidistant between emitter 22 and a receiver 24. The correct angling of C-arm 26 about point 34 is accomplished as follows.

As is seen in FIG. 4, when the image intensifier is positioned as shown in FIGS. 1 and 3, images of adjacent vertebrae 17 and 19 will be seen. Receiver 24 is covered with reticle 25 which has radiopaque indicia, for example, crosshairs 40 and 42 as shown in FIG. 7. Being radiopaque, crosshairs 40 and 42 will also appear on the image viewed by the system operator.

Adjusting the vertical and horizontal position of C-arm 26 of image intensifier 20 will enable the image of the intersection point of crosshairs 40 and 42 to be positioned between adjacent vertebrae 17 and 19 collinear with point 34 when the C-arm is positioned to take a lateral view as illustrated in FIGS. 1 and 4.

Figure 6:
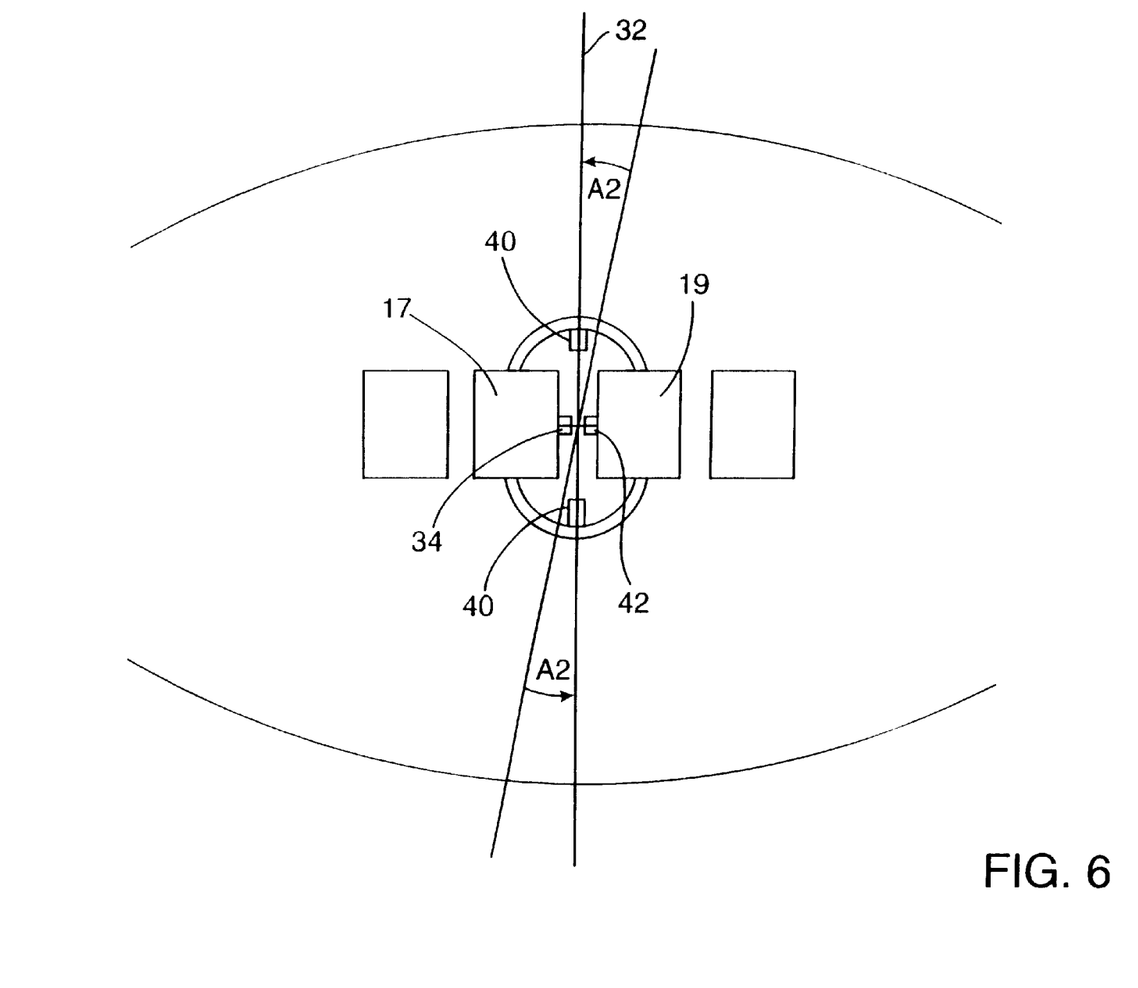
FIG. 6 is a view of an image taken by the image intensifier with the image intensifier being positioned as shown in FIGS. 2 and 5.

Similarly, adjusting the vertical and horizontal position of C-arm 26 of image intensifier 20 will enable the image of the intersection point of crosshairs 40 and 42 to be positioned between adjacent vertebrae 17 and 19 collinear with point 34 as shown when the C-arm is positioned to take an anterior-posterior view as illustrated in FIGS. 2 and 6. In order to align C-arm 26 in the anterior-posterior view of FIGS. 2 and 6, C-arm 26 can be rotated by oblique angle A2.

When crosshairs 40 are aligned in the intervertebral plane in both lateral and anterior-posterior images, rotation of C-arm 26 in its plane of rotation (ie: plane 21 which is co-planar with the plane defined by crosshair 40 on reticle 25, about point 34), will align the C-arm for rotation in a plane which is co-planar to the patient's intervertebral plane. Specifically, when reticle 25 is initially attached to receiver 24, crosshairs 40 are pre-aligned to be coplanar with the plane of rotation of C-arm 26 as is shown in FIG. 7.

After aligning radiopaque crosshairs 40 with intervertebral plane 32, the image intensifier can then be rotated to any position in plane 30 about point 34, (which is also viewable as the intersection point of crosshairs 40 and 42), including an anterior-posterior orientation as is shown in FIGS. 3 and 5, thus aligning C-arm 26 of image intensifier 20 with the intervertebral plane 30.

Once positioned as is shown in FIGS. 1 and 3, image intensifier 20 can then be easily rotated into the position shown in FIGS. 2 and 5 with C-arm 26 remaining in plane 30 to take an anterior-posterior image.

It is to be understood that alignment of image intensifier 20 with plane 32 can also be accomplished first with the image intensifier positioned to take an anterior-posterior view. For example, FIG. 6 shows an illustration of the image intensifier view through adjacent vertebrae 17 and 19 taken along intervertebral plane 30 when the image intensifier is positioned in the orientation shown in FIGS. 2 and 5. Subsequently, image intensifier 20 can be easily rotated to take a lateral view while C-arm 26 remains in the selected intervertebral plane 30. Alignment of the image intensifier with the selected intervertebral plane can also be accomplished at positions between lateral and anterior-posterior orientations.

Figure 8:
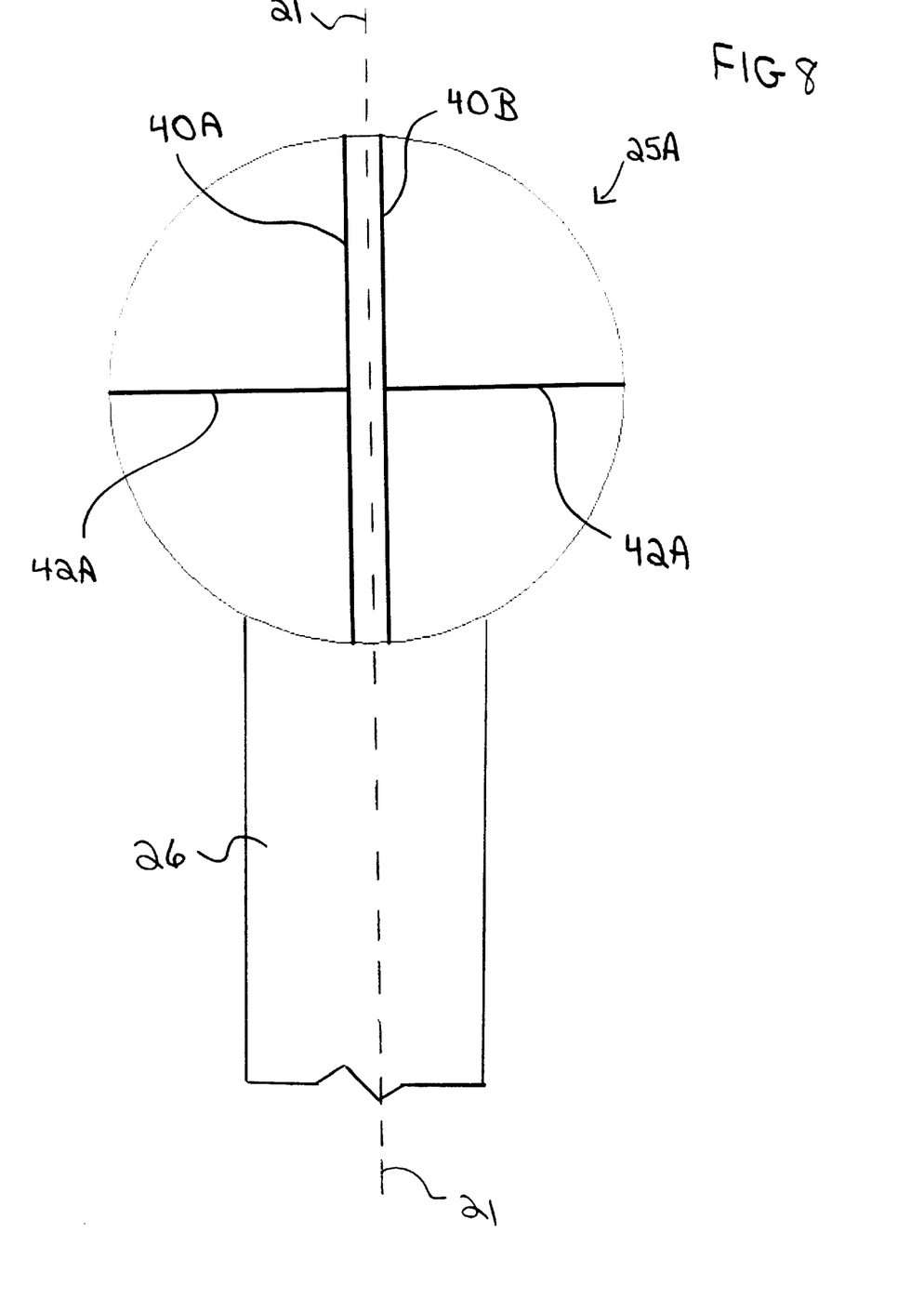
FIG. 8 is an end view of another reticle of the present invention as attached over the receiving end of the image intensifier.
Figure 9:
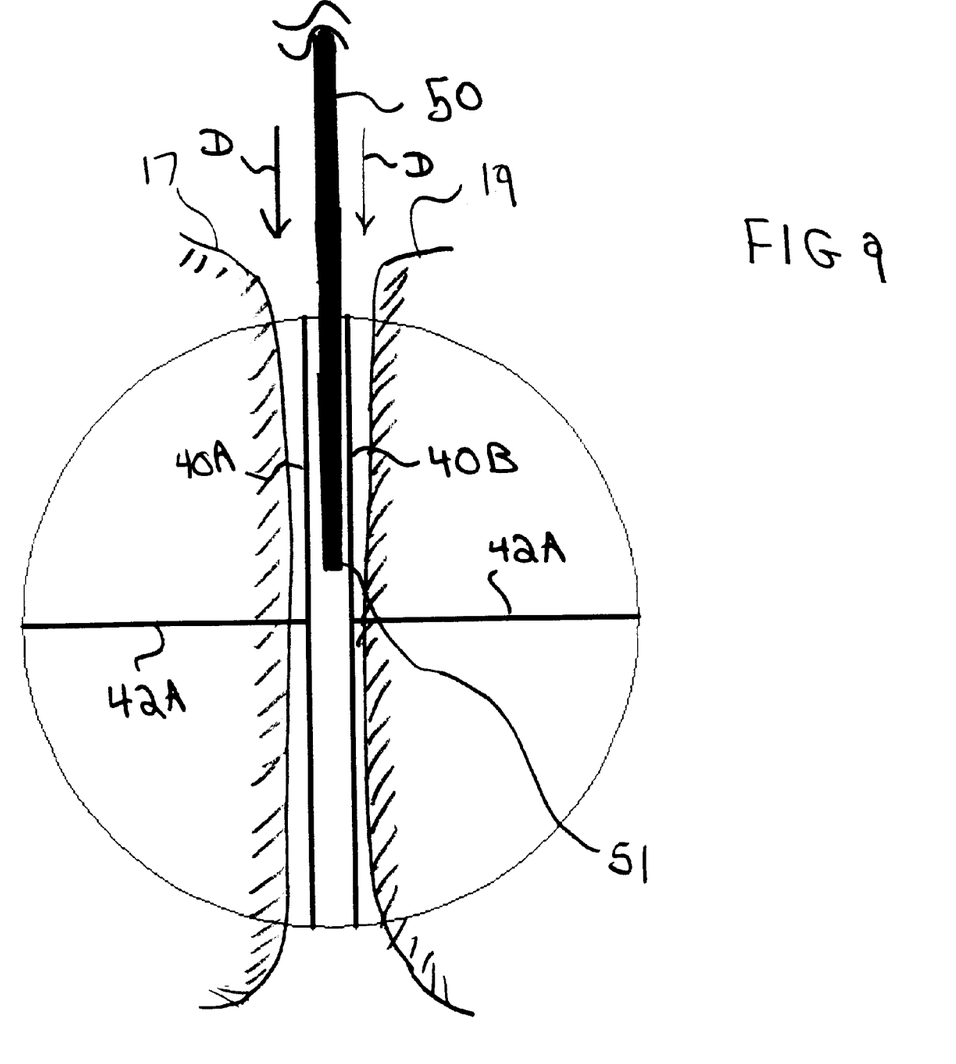
FIG. 9 is a schematic illustration of a surgical instrument being advanced toward an operative site in the patient, as viewed by a surgeon through the reticle of FIG. 8.

FIGS. 8 and 9 show an improved reticle system in which reticle 25A has a pair of parallel indicia 40A and 40B, on opposite sides (an equidistantly from) the center of the reticle. A perpendicular indicia 42A is also provided, as shown. Perpendicular indicia 42A preferably does not cross fully across the center of reticle 25A, as shown.

Reticle 25A is operated in the same manner as reticle 25, as explained above. However, the placement of indicia 40A, 40B and 42A provide further advantages over crosshairs 40 and 42, for example, as shown in FIG. 9 in which a surgical instrument 50 is advanced to an operative site in the patient (e.g.: a site at the center of reticle 25A).

Specifically, as instrument 50 is advanced in direction D, it passes between indicia 40A and 40B. Thus, indicia 40A and 40B can be used to guide the path of instrument 50, with the distal end 51 of instrument 50 passing across the image of the operative site which the surgeon is viewing through reticle 25A. Accordingly, by advancing instrument 50 in a preferred path between indicia 40A and 40B, the motion of instrument 50 within the patient's intervertebral plane can be maintained (when the patient's intervertebral plane 30 is positioned in alignment between indicia 40A and 40B).

Therefore, should end 51 of instrument 50 cross over either of indicia 40A or 40B, this would indicate movement away from the intervertebral plane 30 passing between vertebrae 17 and 19.

In addition, when parallel indicia 40A and 40B are optionally preferably spaced apart a distance approximately equal to the spacing between a patient's vertebrae 17 and 19, indicia 40A and 40B can easily be aligned with (i.e.: placed over the top of, or placed near or adjacent to) the ends of vertebrae 17 and 19 as shown in FIG. 9. This alignment of vertebrae 17 and 19 with indicia 40A and 40B also assists in keeping the movement of instrument 50 in a path which remains between indicia 40A and 40B (i.e.: coplanar with, or very near to, the patient's intervertebral plane 30).

A further advantage of the present invention is that indicia 42A optionally does not pass fully across the center of reticle 25A. By not passing through the center of reticle 25A, visibility of the operative site (which is preferably located directly at the center of reticle 25A) is not obstructed. Instead, the intersection of indicia 42A with both of indicia 40A and 40B assists in centering distal end 51 of instrument 50 at the patient's operative site.

As was explained with reference to reticle 25, reticle 25A is also preferably affixed to C-arm 26 such that indicia 40 (or 40A and 40B) are aligned parallel with plane 21, being the plane of rotation of the C-arm (i.e.: the plane in which C-arm 26 is disposed).

In accordance with the present invention, reticles 25 and 25A may be generally planar, having a flat radio-transparent portion with crosshairs or indicia 40 and 42 or 40A, 40B and 42A being imprinted or marked thereon, or otherwise attached directly thereto. As such, crosshairs or indicia 40 and 42 or 40A, 40B and 42A can comprise lines drawn onto the reticle, or wires attached to the surface of the reticle.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A reticle for attachment to an image intensifier receiver forming part of an image intensifier system having a plane of rotation, comprising:

a flat radio-transparent portion;

a pair of first indicia disposed on the surface of the flat radio-transparent portion, the first indicia being disposed parallel to one another on opposite sides of the center of the radio-transparent portion and parallel to the plane of rotation of the image intensifier system;

a second indicia disposed on the surface of the radio-transparent portion, the second indicia positioned to indicate the center of the radio-transparent portion.

* * * * *